US00PP08335P

United States Patent [19]

Bull

[11] Patent Number: Plant 8,335

[45] Date of Patent: Aug. 3, 1993

[54] IMPATIENS PLANT NAMED ROSEMARIE

[76] Inventor: Norbert Bull, Gärtnersiedlung 2, 2351 Gönnebek, Fed. Rep. of Germany

[21] Appl. No.: 802,860

[22] Filed: Dec. 6, 1991

[51] Int. Cl.[5] ..... A01H 5/00
[52] U.S. Cl. ..... Plt./87.6
[58] Field of Search ..... Plt./87.6

*Primary Examiner*—James R. Feyrer
*Attorney, Agent, or Firm*—Foley & Lardner

[57] ABSTRACT

An impatiens plant named Rosemarie characterized by its bicolored flowers having a carmine rose base color infused with a lighter rose-pink, compact growth habit, small dark green foliage, very floriferous habit, and its suitability for pot plant, patio or bedding plant culture.

2 Drawing Sheets

The present invention relates to a new and distinctive cultivar of impatiens plant, botanically known as Impatiens, and referred to be the cultivar name Rosemarie. The new cultivar was developed by me through controlled breeding by crossing seed or female parent identified as Seedling No. 18 with male or pollen parent identified as Seedling No. 14. Both parents are unreleased and propriety lines.

Asexual reproduction of the new cultivar by the inventor by terminal or stem cuttings taken at Gönnebek, Federal Republic of Germany has shown that the unique features of this new impatiens are stabilized and are reproduced true to type in successive propagations.

The following characteristics distinguish the new impatiens from both its parent varieties and other cultivated impatiens of this type known and used in the floriculture industry:

1. Slightly bicolored flower petals of carmine rose and a lighter rose-pink.
2. Compact grown habit.
3. Small, dark green foliage.
4. Very floriferous habit.
5. Suitable for pot plant, patio or bedding plant culture.

Rosemarie has a main flower color similar to the flower color of the cultivar Sesia. However, Rosemarie is slightly bicolored, it has a quicker growth habit, and there is no yellow variegation in the foliage.

The accompanying colored photographs illustrate the overall appearance of this cultivar, showing the colors as true as it is reasonably possible to obtain in a colored reproduction of this type.

The photo at the top of sheet 1 comprises a top perspective view of a potted plant of Rosemarie.

The bottom photo on sheet 1 shows a single flower (top side), and top and bottom views of a typical leaf.

The photograph on sheet 2 shows the upper side and under side of typical flowers, a bud with attached spur, and the upper side and bottom side of typical leaves. Scales in the centimeters are included to show the size of these parts.

The following is a detailed description of my new impatiens cultivar based on plants produced under normal commercial practice at Gönnebek, Federal Republic of Germany.

Color references are made to the Royal Horticulatural Society (R.H.S.) Colour Chart except where general terms of ordinary dictionary significance are used.

Parentage: Controlled cross between Bull Unnamed Seedling No. 18×Bull Unnamed Seedling No. 14.

Propagation:

*Type cutting.*—Stem 15–20 mm long will grow to 4–5 cm in 20 days.

*Time to initiate roots.*—8 days at 22° C. summer. 10 days at 20° C. winter.

*Rooting habit.*—Very good.

Plant description:

*Form.*—Symmetrically mounded, self-branching.

*Habit of growth.*—Compact growth habit. Eight (8) weeks after sticking stem cuttings in 12 cm pots, plant is approximately 30 cm in diameter and 32 cm in height, measured from top of pot.

*Foliage description.*—(1) Size: Relatively small. Length is approximately 8–10 cm, and width approximately 4 cm at point of maximum width. (2) Shape: Generally ovate, with acute to acuminate tip and rounded to acute base; see photos. (3) Margin: Mildly serrated. (4) Color: (a) Young foliage upper surface: Dark green, darker than RHS 139A). (b) Under surface: Reddish green, no accurate color value represented. (c) Mature foliage upper surface: Dark green, darker than RHS 139A. (d) Under surface: Base color approximately 191B-C, but heavily infused with red to provide an overall color not represented on the color chart. (5) Veination: Red veins on under side (see photo). (6) Variegation: None.

Flowering description:

*Flowering habit.*—Flowers from leaf whorl in uniform manner.

*Natural flowering season.*—March until October.

*Flower buds.*—Typical; brown red in color.

*Flowers borne*—On pedicels red-purple in color.

*Quantity of flowers.*—Very floriferous. Flowers both mask the crown and occur above the leaf canopy.

*Spur.*—Downwardly curved from base of calyx, approximately 4–5 cm in length and red-purple in color.

*Longevity.*—Flowers are long lasting and non-fading.

*Petals.*—Number of petals: Five (5). Shape: Generally heart-shaped (see photo). Color: Upper Surface: Main color 47C infused with 49A to give bicolor effect, with center eye of 58B and tinging of 58B-C along midveins of petals. Under surface: Same as for top side, only slightly lighter.

Size of flower: Medium, approximately 6 cm. diameter.

Reproductive organs:

*Stamens.*—Five (5).

*Anthers.*—Hooded, pink in color.

*Pollen color.*—White.

*Stigman.*—Five in number, red in color.

*Styles.*—Red in color.

*Ovary.*—5 in number, size 3–5 mm., brown-red in color.

Disease resistance: No disease problems noted to date.

I claim:

1. A new and distinct impatiens plant named Rosemarie, as illustrated and described.

* * * * *

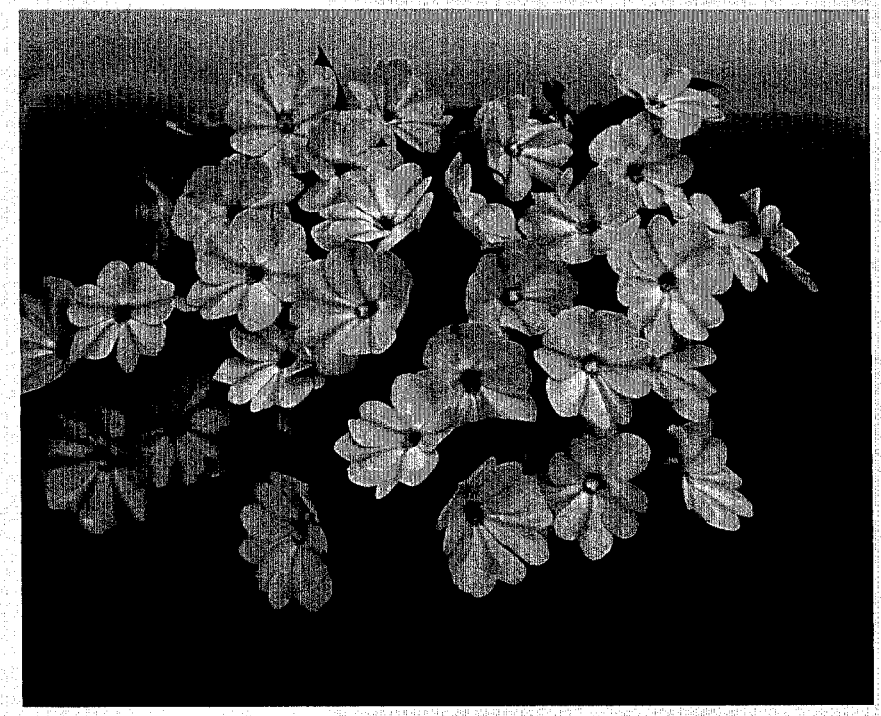
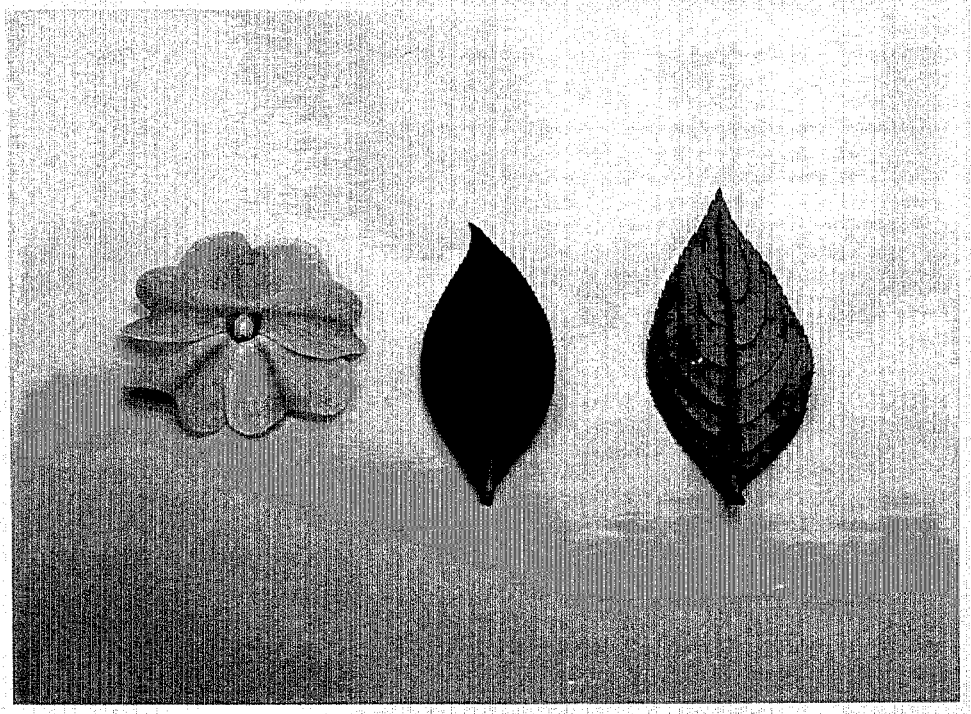

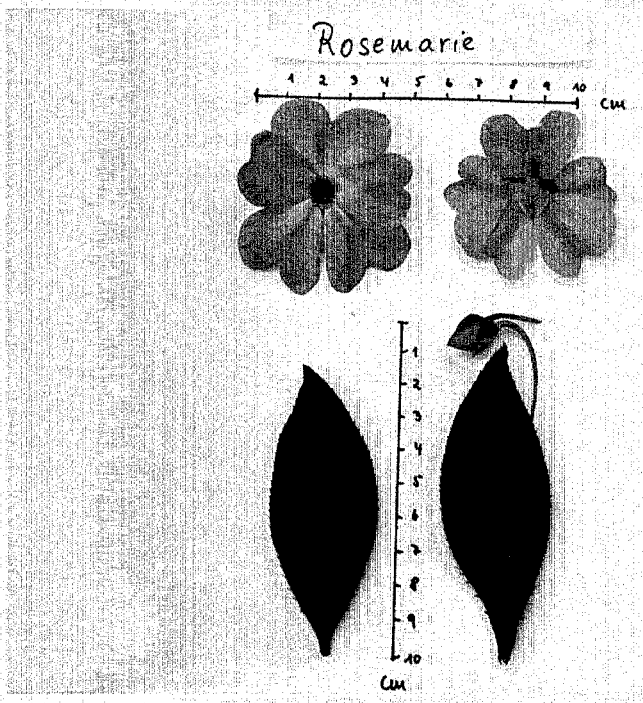
Rosemarie
1 2 3 4 5 6 7 8 9 10
cm
1 2 3 4 5 6 7 8 9 10
cm